(12) United States Patent
Stefano et al.

(10) Patent No.: US 8,017,146 B2
(45) Date of Patent: Sep. 13, 2011

(54) TRANSDERMAL DELIVERY SYSTEM WITH TWO SUPERIMPOSED ADHESIVE LAYERS HAVING DIFFERENT AFFINITIES TO THE ACTIVE SUBSTANCE COMPRISED

(75) Inventors: Francisco Jose Evaristo Stefano, Buenos Aires (AR); Alejandro Fabio Scasso, Buenos Aires (AR)

(73) Assignee: Amarin Technologies S.A., Buenos Aires (AR)

( * ) Notice: Subject to any disclaimer, the term of this patent is extended or adjusted under 35 U.S.C. 154(b) by 1278 days.

(21) Appl. No.: 10/514,047

(22) PCT Filed: May 15, 2003

(86) PCT No.: PCT/GB03/02118
§ 371 (c)(1),
(2), (4) Date: May 20, 2005

(87) PCT Pub. No.: WO03/097020
PCT Pub. Date: Nov. 27, 2003

(65) Prior Publication Data
US 2005/0208116 A1  Sep. 22, 2005

(30) Foreign Application Priority Data
May 15, 2002  (AR) ................. P020101791

(51) Int. Cl.
*A61K 9/00* (2006.01)
*A61F 13/00* (2006.01)
*A61F 13/02* (2006.01)

(52) U.S. Cl. .................. 424/449; 424/447; 424/448

(58) Field of Classification Search .................. 424/449, 424/448
See application file for complete search history.

(56) References Cited

U.S. PATENT DOCUMENTS

| 4,031,894 A | 6/1977 | Urquhart et al. |
| 4,060,084 A | 11/1977 | Chandrasekaran et al. |
| 4,201,211 A | 5/1980 | Chandrasekaran et al. |
| 4,262,003 A | 4/1981 | Urquhart et al. |
| 4,286,592 A | 9/1981 | Chandrasekaran |

(Continued)

FOREIGN PATENT DOCUMENTS
WO  WO-00/41538  7/2000

(Continued)

OTHER PUBLICATIONS

Fiset, et al., "Biopharmaceutics of a New Transdermal Fentanyl Device," *Anesthesiology*, vol. 83(3) (Sep. 1995): 459-469.

*Primary Examiner* — Anand Desai
*Assistant Examiner* — Melissa Mercier
(74) *Attorney, Agent, or Firm* — Stites & Harbison PLLC; Marvin Petry; Stephen J. Weyer

(57) ABSTRACT

A device for the transdermal delivery of a pharmacologically active substance has first and second superimposed mutually contacting adhesive layers (2, 3). The first layer (3) is in use brought into contact with the skin. The active substance is dissolved in both layers, the affinity of the first layer for the active substance being between about 1.15 and about 10 times lower than that of the second layer. The percent saturation of the active substance in both the layers is the same and is less than 100%. The first layer has a greater thickness than the second layer. The device is simple and can provide stable delivery over a long period.

22 Claims, 4 Drawing Sheets

U.S. PATENT DOCUMENTS

| | | | |
|---|---|---|---|
| 4,436,741 | A | 3/1984 | Urquhart et al. |
| 4,769,028 | A | 9/1988 | Hoffmann et al. |
| 4,906,463 | A | 3/1990 | Cleary et al. |
| 4,938,759 | A | 7/1990 | Enscore et al. |
| 5,004,610 | A | 4/1991 | Osborne et al. |
| 5,006,342 | A | 4/1991 | Cleary et al. |
| 5,230,898 | A * | 7/1993 | Horstmann et al. ......... 424/449 |
| 5,310,559 | A | 5/1994 | Shah et al. |
| 5,474,783 | A | 12/1995 | Miranda et al. |
| 5,656,286 | A | 8/1997 | Miranda et al. |
| 5,662,926 | A * | 9/1997 | Wick et al. ................ 424/448 |
| 5,958,446 | A | 9/1999 | Miranda et al. |
| 6,024,976 | A | 2/2000 | Miranda et al. |
| 6,074,665 | A | 6/2000 | Horstmann et al. |
| 6,174,545 | B1 | 1/2001 | Enscore et al. |
| 6,221,383 | B1 | 4/2001 | Miranda et al. |
| 6,235,306 | B1 | 5/2001 | Miranda et al. |
| 2004/0202704 | A1 | 10/2004 | Sharma et al. |

FOREIGN PATENT DOCUMENTS

| | | |
|---|---|---|
| WO | WO-01/26705 | 4/2001 |
| WO | WO-01/39754 | 6/2001 |
| WO | WO-02/26217 | 4/2002 |
| WO | WO 0226217 A2 * | 4/2002 |
| WO | WO-2004/098472 | 11/2004 |

* cited by examiner

TRANSDERMAL DELIVERY SYSTEM WITH TWO SUPERIMPOSED ADHESIVE LAYERS HAVING DIFFERENT AFFINITIES TO THE ACTIVE SUBSTANCE COMPRISED

FIELD OF THE INVENTION

The present invention relates to transdermal delivery devices for the transdermal administration of active substances, such as pharmacologically active substances, and to the manufacture of such devices.

BACKGROUND TO THE INVENTION

The advantages of the transdermal administration of drugs over other routes are well known. Nevertheless, the skin permeation of the majority of the drugs is not enough to provide suitable therapeutic levels. The skin, particularly the stratum corneum, provides a barrier for the permeation of many substances. Several alternatives have been proposed to solve this problem, most of them based on the use of a suitable permeation enhancer.

In comparison with the conventional administration routes of potent drugs, the transdermal administration offers important advantages. The main reasons are its simplicity and that the administration is not invasive. Moreover, those devices have more bioavailability than the oral route because the drug avoids the first pass through the digestive system where it is sometimes metabolised or inactivated in significant proportions. Besides, its administration can be immediately interrupted if side effects are detected.

Generally, the transdermal route of administration offers the potential benefits of simplicity, efficacy and acceptability by the patient. This acceptance is essential for any treatment with this type of devices and so they must be substantially comfortable: they should not be bulky, they should be aesthetically pleasant to sight and touch, should be maintained correctly affixed to the patient's skin during the period of use and should be easily detached when required.

Theoretically, transdermal administration devices should provide a steady plasmatic concentration during an extensive period of time, with an acceptable variability between patents. The physicochemical and physiological principles that governs the absorption of drugs through the transdermal route are well known.

In the literature several devices have been described for the transdermal administration of drugs.

The skin is, generally, an effective barrier for the permeation of drugs and the diffusion of them is slower than through other membranes of the organism. The simple occlusion of the skin by means of non-permeable barriers increases the hydration of the stratum corneum, increasing markedly the permeation of drugs compared to the skin without occlusion.

Further the vehicle in which the drug is dissolved can also contribute to determine the extent of absorption. The addition permeation enhancers can increase several fold the absorption of some drugs. The term "penetration" is used for the income of the drug to the skin and "permeation" for the process of crossing the skin and arrival to the circulation, even though there is not an absolute demarcation between both processes.

The transdermal delivery devices should be formulated so that the contained drugs have a penetration and a permeation according to the propose of the product.

Nowadays there are different types of transdermal devices. Nevertheless, these devices could be grouped in two main categories: reservoir-type devices and matrix-type devices. In the literature other types of device have been described, but all of them could be considered as extensions of one of these groups or as combinations of them.

The transdermal devices of reservoir-type contain a reservoir that contains the active pharmaceutical ingredient (API). From that reservoir, the API diffuses through the controlling membrane to the site of absorption. The controlling membrane could be microporous or continuous. These devices usually have a backing layer, a reservoir that contains the drug, a controlling membrane, an adhesive layer and a release or protective layer. The main advantage of this type of device is that the rate of drug delivery is maintained practically constant for long periods of time. Nevertheless, these devices are usually bulky (voluminous), they have a total surface that is bigger than the active surface and, besides, they have the disadvantage that the rupture of the controlling membrane could produce a higher release than desired.

There are several transdermal devices of this type in the market, which differ from each other in the reservoir of the drug. The reservoir can be a polymer, a liquid, a gel or a cream, in which the drug is dissolved or dispersed.

Within the group of patches with reservoir, the transdermal devices with multireservoirs with controlling membrane as well as the devices with reservoir and without controlling membrane can be included. The main characteristic of the first type is that the permeation enhancer agent is stored in a compartment separated from the drug reservoir and that of the second type is that an adhesive layer not loaded with drug functions as the control of the permeation.

On the other hand, matrix-type transdermal devices comprise, generally, a nonpermeable backing liner, a polymeric adhesive matrix in which the active drug or drugs are dissolved or dispersed and a release liner. They have a total surface area that is the same as that of the active surface. Generally, this type of device has had greater acceptance by patients than the reservoir-type patches.

The current trend in the design of transdermal delivery devices is directed to matrix-type devices. This is not only because the production costs are lower, but because it is possible to obtain devices with greater versatility than the reservoir-type ones.

One disadvantage of the matrix-type devices is that, for some active substances, it is difficult to maintain a constant dose for extended periods of time. Generally, in this type of device, the delivery rate diminishes with the time as a consequence of the decrease of the concentration of the API in the matrix.

The addition of polymeric layers acting as controlling membranes for the drugs has not been completely successful because they are usually less comfortable to use by the patient, mainly because their mechanical properties became worse with the mentioned addition. Another problem to be solved in this type of device is the one related to physical stability because, generally, to assure a constant delivery, the active substance needs to be present in a saturation or supersaturated concentration. Besides, it is important for the comfort of the user that the size of the device should be as small as possible.

Finally, it is very important that the transdermal device has enough adhesiveness to be able to remain on the application site assuring suitable drug delivery during the necessary period of time, while having, at the same time, a painless removal, which is not easy to obtain.

In literature several documents that disclose devices for transdermal administration comprising two or more adhesive layers can be found.

As examples, U.S. Pat. No. 4,031,894, U.S. Pat. No. 4,060,084, U.S. Pat. No. 4,262,003, U.S. Pat. No. 4,436,741 and U.S. Pat. No. 4,201,211 (Alza Corporation) disclose devices with reservoir and rate controlling membrane for the transdermal administration of drugs that deliver an initial pulse followed by a substantially constant dosage. According to those documents, the preferred embodiment consists in a therapeutic system in the form of a bandage with four layers that comprise: a) a protective backing layer, b) a reservoir layer that comprises the a pharmaceutical active drug (for example scopolamine, clonidine, etc.) dispersed in a mixture of a mineral oil gel and polyisobutylene, c) a microporous membrane that control the rate at which the drug is released and d) an adhesive layer.

U.S. Pat. No. 5,310,559 (Hercon Laboratories Corporation) disclose devices with reservoir and controlling rate membrane with a structure similar to the ones already mentioned that include the use of the copolymers of acrylate-olefin as control rate membrane of the active substances.

U.S. Pat. No. 5,004,610 (Alza Corporation) discloses a device with reservoir and controlling rate membrane, for the administration of nicotine. According to the disclosure, nicotine is dissolved within said reservoir in a solvent (preferably a copolymer of ethylene-vinyl acetate) with a concentration below its saturation.

All the devices in the documents above mentioned belong to the type "with reservoir and controlling rate membrane" and present the disadvantages and objections previously mentioned. It is important to note that for the controlled drug flux, these devices need the addition of a controlling membrane and cannot perform adequately without it. The membrane is located between the drug and the adhesive layer and it is a fundamental element of the device.

The use of adhesive polymers acting as controlling rate membranes or a control of the final flux of the drug to the skin has been described.

On the other hand, U.S. Pat. No. 4,769,028 (Lohmann GmbH & Co.) disclose a device that comprises a reservoir containing several layers, in which the concentration of the drug is supersaturated and increases layer to layer, as the distance to the adhesive layer increases. According to the disclosure, the layers of said reservoir can have the same polymeric composition.

U.S. Pat. No. 4,938,759 (Alza Corporation) discloses a device for the transdermal administration of drugs moderately soluble in mineral oil and that have a melting point higher than 50° C., comprising a reservoir layer that consists of a dispersion of the drug in a ethylene-vinyl acetate copolymer in a concentration higher than saturation. In the same way, U.S. Pat. No. 6,174,545 (Alza Corporation) and U.S. Pat. No. 6,074,665 (LTS Lohmann Therapie-Systeme GMBH) require that the drug should be dispersed under supersaturated concentrations.

The main disadvantage of this type of device is the use of high amounts of drug to supersaturate all the layers. As a consequence, the supersaturation can make the device unstable, producing the crystallisation of the drug and making the device physically unstable. Moreover, the necessity of using many layers, as for example the ones required for the device disclosed in U.S. Pat. No. 4,769,028, produce an increase of the final thickness of the device that impairs its mechanical properties. Finally, this type of device needs also a complex and extensive manufacture process that can raise the production costs and consequently the price of the final product.

On the other hand, U.S. Pat. No. 4,906,463 and U.S. Pat. No. 5,006,342 disclose the use of a multiplicity of spaced structural layers, to provide better mechanical properties in a device for transdermal administration. The main disadvantage of this type of device is that it often presents a high inter-patient variability for the delivery of the drug, which makes it unsuitable for treatments with drugs whose application window should be strictly fixed (see for example Anesthesiology, 83, 459-469 (1995)).

WO 0126705 (Samyang Corporation) disclose a device for the transdermal administration of drugs that comprises two layers of adhesive, wherein each layer is positioned adjacent to the other, containing each one the same drug and being both laminated over the same backing layer.

Additionally, WO 0139754 (Pierre Fabre Medicament) disclose adhesive patches comprising two chambers such that the first chamber is a reservoir-type transdermal device and the second chamber is matrix-type transdermal device located at the periphery of the first chamber. Said two chambers contain the same active substance.

Both aforementioned WO applications describe products that are difficult to manufacture. Besides, as each layer functions independently, both of them should be in contact with the skin, increasing the surface of the device.

Additionally, it has been described that, in order to achieve optimal adhesive or retention properties, it possible to combine commercial adhesives to obtain better formulations. In those prior art documents, it has been stated that using certain mixtures it is possible to modulate the amount of drug to be used or to increase or diminish the drug flux of the active drug (see for example U.S. Pat. No. 5,474,783, U.S. Pat. No. 5,656,286, U.S. Pat. No. 5,958,446, U.S. Pat. No. 6,024,976, U.S. Pat. No. 6,221,383, U.S. Pat. No. 6,235,306, WO 0041538).

WO 02/26217 describes, but does not exemplify, a transdermal drug delivery device having two layers of different composition and a backing layer, called an adhesive rate controlled system. The layer adhered to the backing is a drug reservoir and the other layer is a rate controlling layer which in use contacts the skin. The two layers have different affinity for the drug, the skin-contacting layer having a lower affinity. The difference of affinity allows the delivery rate to be controlled.

SUMMARY OF THE INVENTION

Accordingly, one of the objects of the present invention is to provide an adhesive matrix-type device for the transdermal administration of an API, which is physically and chemically stable and provides delivery of a suitable amount of drug for an extended period of time.

Another object of the invention is to provide an adhesive matrix-type device for the transdermal administration of an API that provides a suitable delivery for therapy without using a rate controlling membrane for the delivery of the API.

Another object of the invention is to provide an adhesive matrix type device for the transdermal administration of an API with good mechanical properties and a suitable surface for the tolerance of the patient.

Another object of the invention is to provide an adhesive matrix-type device for the transdermal administration of an API that gives within acceptable limits a constant and predictable flux.

Finally, another object of the invention is to provide a simple procedure for manufacture of an adhesive matrix-type device, for the transdermal administration of active substances.

The present invention solves the problems described above by means of a transdermal delivery device that comprises two superimposed adhesive layers. Devices of the invention can show a suitable and stable permeation over a long period of time without requiring high concentrations of drugs that would imply wasting (misspending) of the active substance and possible physical instability. This is especially useful for drugs of high cost.

Without intending to be restricted to any particular theoretical explanation, we understand that, where a functional polymer is employed in the layer that acts as reservoir in the present invention, a chemical interaction of an energy higher than the attractive intermolecular forces required for a simple solubility interaction, between the functional group of the polymer and the active drug, may exist.

Surprisingly, we have found that by the use of two adhesive layers of selected thickness and affinity for the delivered active substance, both adhesive layers containing an initial amount of active drug in a particular concentration, it is possible to obtain a matrix type device with desirable characteristics.

The superposition of the two adhesive layers of different thickness, composition and interaction with the drug gives as a result a device of particular useful characteristics, which may not be predictable from the individual behaviour (performance) of each layer and are not predictable from the resulting behaviour of the combination of these adhesives in a single layer. The devices of the present invention can obtain a constant and controlled delivery over the time.

According to the invention there is provided a transdermal delivery device for the transdermal delivery of an active substance, for example a pharmacologically active substance, the device having first and second superimposed mutually contacting adhesive layers, of which the first layer is pressure sensitive adhesive and is in use brought into contact with the skin, the active substance being dissolved in both layers, wherein the affinity of the first layer for the active substance is between about 1.15 and about 10 times lower than that of the second layer, the percent saturation of the active substance in both layers being the same and being less than 100%, the first layer having a greater thickness than the second layer.

The device thus has a first layer made of a pressure sensitive adhesive and a second layer made of a pressure sensitive adhesive or a mixture of pressure sensitive adhesives, in which one or more active substances are dissolved, where each layer presents a different adhesive composition and a different affinity for the active substance or substances and where each adhesive layer has a similar saturation level of less than 100%. The term "percent saturation" expresses the concentration of the active substance in the adhesive matrix layer as a percentage of the maximum concentration (saturation) at a given temperature, e.g. room temperature.

In this way, in the two-layered device of the present invention, the first layer is designed to be in close contact with the skin of the patient and is the one that delivers the necessary dose of active substance to obtain the desired pharmacological action, while the second layer is effective to replenish the loss of active substance from the first layer when the device is in contact with the skin. We have found that the use of a first layer which is thicker than the second one enables us to obtain a suitable drug delivery profile with a low or minimum total drug load, thus optimising product cost. The role of the second layer is to replenish the first layer with drug, as it is lost from the first layer to the patient, thus achieving a highly constant efflux rate during the period of use. With its higher drug load, the second layer is thinner.

Although it is preferred that the present invention relates to devices for the transdermal administration of active substances during continuous long periods of time, in which the limitation to the passage of the drug is the skin of the patient, the device can also control by itself the delivery of the drug.

The device of the invention can be used for the administration of active substances selected from the group of the opioid analgesics and their pharmaceutical active derivatives and analogues (fentanyl, alfentanyl, sufentanyl, arfentanyl, lofentanyl, buprenorphine; nalbuphine, butorphanol and oxicodone). The device of the invention is especially useful for the transdermal administration of fentanyl.

The device of the present invention can be used for the transdermal administration of a combination of analgesics, particularly of the ones that belong to the group that consists on fentanyl and its pharmaceutically acceptable salts or derivatives. Fentanyl is a well known substance and its pharmacological activity, side effects and recommended administration dose can be found in specialised literature. See for example *Physician's Desk Reference*, *The Merck index* and *The Martindale Extra Pharmacopoeia*. The term fentanyl, as well as the designation of each other active compound mentioned in the present application, include also all of its pharmaceutically acceptable derivatives, including its salts and enantiomers.

Other active substances that can be administered effectively by the device of the present invention are for example an agent for the treatment of the tobacco abstinence as for example nicotine, analgesic and anti-inflammatory agents, anaesthetics as for example xylocaine, agonists as for example salbutamol, procaterol and anticolinergics as for example scopolamine.

The device according to the present invention can be particularly useful to administer therapeutic drug combinations of two or more active compounds as for example nalbuphine/fentanyl, butorphanol/sufentanyl, buprenorphine/fentanyl, oxicodone/ketorolac trometamol and buprenorphine/ketorolac trometamol.

The mentioned combinations present advantages principally because the difference between the pharmacokinetics of each drug of the combination may allow a faster beginning of the action and, at the same time, a longer lasting effect than that obtained by a device with a single substance.

The active agents are not limited to the aforementioned examples and the device can be used for the administration of cosmetically active substances. The amount of active substance is not limited to any specific range, but varies according to the active substance to be used and can be determined by those skilled in the art depending on the purpose of the use of the device, for example the amount of active drug can vary between 0.1 and 40% of weight based on the total weight of the adhesive layers.

Preferably, a device for the transdermal administration of fentanyl according to the invention, initially comprises between about 2 and about 4% of fentanyl in the layer to be in contact with the skin and between about 4 and about 10% of fentanyl in the second layer, expressed as percentages of the dry weight of each of the adhesive layers.

The initial concentration given here refers to the state when the device is ready for use.

Also preferably, a device for the transdermal administration of nicotine according to the present invention initially comprises between about 2 and about 12% of nicotine in the layer to be in contact with the skin and between about 5% to about 25% of nicotine in the second layer, expressed as percentages of the dry weight of each of the adhesive layers.

According to a particular embodiment of the invention, a device for the transdermal administration of sufentanyl initially comprises between about 0.2 and about 2% of sufentanyl in the layer to be in contact with the skin and between about 5% to about 25% of sufentanyl in the second layer, expressed as percentages of the dry weight of each of the adhesive layers.

In another particular embodiment of the invention, a device for the transdermal administration of alfentanyl initially comprises between about 1 and about 9% of alfentanyl in the layer to be in contact with the skin and between about 2% to about 12% of alfentanyl in the second layer, expressed as percentages of the dry weight of each of the adhesive layers.

In the particular case of the drug buprenorphine, a device for the transdermal administration according to the present invention initially comprises between about 1 and about 6% of buprenorphine in the layer to be in contact with the skin and between about 5% to about 12% of buprenorphine in the second layer, expressed as percentages of the dry weight of each of the adhesive layers.

According to a preferred embodiment of the invention, the device comprises a first adhesive layer made of a non-functional pressure sensitive adhesive with a low affinity for the active substance and a second layer made of a functional pressure sensitive adhesive or a mixture of a functional and non-functional pressure sensitive adhesives with a higher affinity and higher power of retention of the active substance. Thus in this embodiment, the adhesive of the first-layer is substantially free of functional groups, but the presence of a small amount of monomeric units carrying functional groups can be tolerated if it does not significantly affect the properties of the layer.

By non-functional pressure sensitive adhesives are meant those polymeric adhesives that do not have reactive functional groups in the polymeric chain and particularly those not having carboxylic (—COOH) and hydroxyl (—OH) groups. It is preferable also to exclude amine (primary, secondary and tertiary), keto and silanol groups, as they may interact with the active substance. Non-limiting examples of this type of adhesives are the following: Acrylics (for example Duro Tak 874098 from National Starch), polyisobutylenes of low and high molecular weight (for example Opanol from BASF), polyisobutylenes (for example L-100 sold by Exxon, 4H, 5H and 6H, sold by Rit-Chem), rubbers of copolymers of styrene, butadiene, isoprene and silicone elastomers (for example SSAs 7-9800 from Dow Corning).

By acrylics, we mean polyacrylate adhesives which are polymers or copolymers of acrylic acid esters or methacrylic acid esters as monomers. Other monomers such as vinyl acetate may be present.

In the same manner, by functional pressure sensitive adhesives are meant those polymeric adhesives that have reactive functional groups in the polymeric chain and particularly those that have carboxylic and hydroxyl groups in said chain. Non-limiting examples of this type of adhesives are the following: i) with —OH groups: Gelva 737 (Solutia Inc.), Gelva 788 (Solutia Inc.), Duro Tak 87-2516, (National Starch), Duro Tak 87-2287 (National Starch), Duro Talc, 87-2510 (National Starch), BIO-PSA 7-440X (Dow Corning), BIO-PSA 7-450X (Dow Corning), BIO-PSA 7-460X (Dow Corning). ii) with —COOH: Duro Tak 87-2051 (National Starch), Duro Tak 87-2154 (National Starch), Duro Tak 87-2353 (National Starch), Duro Tak 87-2852 (National Starch), Duro Tak 87-2100 (National Starch), Duro Tak 87-2070 (National Starch), Gelva 1430 (Solutia Inc.) and Gelva 1753 (Solutia Inc.).

The device of the invention comprises a first adhesive layer that has an affinity for the active substance or substances between about 1.15 to 10 times lower than that of the second layer, preferably 1.15 to 1.75 times lower. The term "affinity" should be understood as the inverse of the efflux drug rate, from the matrix to a suitable aqueous medium, in sink conditions. Those skilled in the art will know, by means of the suitable measurements, how to select the adhesives or mixtures of them that will be suitable to fulfil this requirement, for any particular application of the invention.

Preferably the affinity of said first layer for the active substance is 1.15 to 1.75 times lower than that of the second layer.

The affinity ratio can also be expressed as the solubility ratio.

The thickness of the first layer that will be in contact with the skin should be thicker than the second layer. Generally, the thickness of each dry adhesive layer is in the range between about 5 to about 150 µm. Thus for example the thickness of the first layer when dry is in the range 5 to 125 µm and the thickness of the second layer when dry is in the range 5 to 75 µm. Preferably, the thickness of each dry layer will be between about 10 to about 75 µm.

Preferably the ratio of the thickness of the first layer to the thickness of the second layer is in the range 1.2 to 7.

Preferably the composition of the mixture of pressure sensitive adhesives of the device comprises around 10 and around 90% of the functional adhesive and between around 90 and around 10% of the non-functional adhesive, said percentages based on the total weight of the dry adhesive layer. More preferably, it comprises between around 50 and around 80% of the functional adhesive and between around 50 and around 20% of the non-functional adhesive, said percentages based on the total weight of the dry adhesive layer.

An important optional component of the present invention is the permeation enhancer. Those skilled in the art will know what type of enhancer is suitable to be used and in what amount. Preferably, the enhancers to use in the present invention are selected between the following: i) fatty acids: e.g. stearic, oleic, lauric, myristic, palmitic, linoleic, linolenic, caproic, caprylic, neodecanoic, ii) fatty alcohols: e.g. octanol, decanol, lauryl, myristyl, oleyl, palmityl, iii) lower alcohols: e.g. ethanol, propanol, isopropanol, iv) fatty acid esters: e.g. isopropyl myristate, isopropyl palmitate, ethyl oleate, glyceryl monooleate, propylene glycol monolaurate, v) glycols: e.g. propylene glycol, polyethylene glycol, butylene glycol, vi) terpenes: e.g. D-limonene, menthol, eucalyptol, camphor and vii) others: e.g. azone, water, dimethylsulfoxide, 2-methylpyrrolidine.

By fatty acids and fatty alcohols we mean compounds having preferably 8 to 20 carbon atoms in the chain.

The amount of permeation enhancer that is present in the device of the invention will vary according to the active substance used and according to the desired delivery. Preferably, this amount is in the range comprised between around 3.5 and 22%.

One skilled in the art will be able to select the material for the backing layer to be used in the present invention. Examples not limiting of commercial backing layers are the following: Polyethylene layer with a thickness between 25 to 100 µm (for example CoTran 9720 and CoTran 9711 from 3M), polyolefin layer with a thickness between 25 to 100 µm (for example CoTran 9722 from 3M), ethyl-vinyl acetate layer with a thickness between 25 to 100 µm (for example CoTran 9726 from 3M), pigmented polyester layer with a thickness between 25 to 100 µm (for example Scotchpack 9723 from 3M), ethyl-vinyl acetate layer with a thickness between 25 to 100 µm (for example CoTran 9702 and CoTran 9728 from 3M), polyolefine foam layer with a thickness between 250 to 2000 µm (for example Foam Tape 1777, Foam Tape 1779, Foam Tape 9751 y Foam Tape 9773), polyvinyl-chloride foam layer with a thickness between 250 to 2000 µm (for example Foam Tape 9772L), polyurethane layer with a thickness between 25 to 100 μm (for example Scotchpack 9701 from 3M), multilaminated of aluminised and pigmented polyester, polyethylene and ethyl-vinyl acetate with a thickness between 25 to 100 μm (for example Scotchpack 1006, Scotchpack 1009 and Scotchpack 1109 from 3M), multilaminated of polyester, polyethylene and ethyl-vinyl acetate with a thickness between 25 to 100 μm (for example Scotchpack 1220 from 3M), multilaminated of polyester and ethyl-vinyl acetate with a thickness between 25 to 100 μm (for example Scotchpack 9732 from 3M), cotton, polyester, rayon, nylon and polyurethane, woven and non-woven fabrics.

Likewise, as release liner can be used, among others, the following: siliconised polyester liner with a thickness between 25 to 250 μm (for example 1-5 PESTR 6200 P2, DCP-Lohja and Scotchpack 9742 from 3M), teflonated polyester liner with a thickness between 50 to 250 μm (for example Scotchpack 1022 from 3M) and a siliconised and aluminised polyester with a thickness between 50 to 250 μm (for example 1-3 MET-PESTR 6200 P2 y DCP-Lohja).

To give some examples of sizes of devices of the invention, the total surface of the device is the same of the active area, this surface being smaller than 15 $cm^2$ when the dose of the pharmacological active substance released is 25 μg/h, smaller than 27 $cm^2$ when the dose of the pharmacological active substance released is 50 μg/h, smaller than 36 $cm^2$ when the dose of the pharmacological active substance released is 75 μg/h and smaller than 45 $cm^2$ when the dose of the pharmacological active substance released is 100 μg/h.

Basically, the manufacture of the devices for transdermal administration, also known as matrix adhesive type medically adhesive patches involves, in summary, the following steps:
  a) Preparation of the adhesive mixture: In this step, the components of the formulation are mixed between them in order to obtain a solution or an homogeneous suspension.
  b) Spreading-Drying-Laminating: In these steps, the adhesive mixture is homogeneously spread on a liner with suitable characteristics. This liner, generally, has one treated surface. It can consist of a fine silicone or other material layer that will allow it to detach easily from the adhesive layer in order to expose the adhesive surface of the patch that is fixed to the skin of the user. The obtained spread layer, that generally is not thicker than 1 mm, is then conducted to an area, oven or drying tunnel where the solvents of the adhesive polymer are eliminated, obtaining in this way an adhesive matrix deposited on a liner. Then this is laminated in a process characterised by the deposit of a second layer on the exposed face of the adhesive matrix.
  c) Cutting: In this step the laminate obtained in the previous step is cut in patches with suitable shape and surface.

In a second aspect, the invention particularly provides a process for the manufacture of a device as described above for the transdermal administration of an active substance, which comprises the following steps:
  a. coating and drying a first precursor adhesive layer that will be the second layer of said device onto a temporary release liner;
  b. laminating said first precursor adhesive layer together with the temporary release film onto a backing layer;
  c. coating and laminating onto a final release liner a second precursor adhesive layer that will be the first layer of said device; and
  d. detaching the temporary release film and laminating said second precursor adhesive layer adhered to the final release liner obtained in (c) to said first precursor adhesive layer obtained in (b) that is adhered to the backing layer.

Suitably the respective amounts of said active substance in said first and second precursor adhesive layers differ from the amounts in said device when ready for use, and after step (d) the active substance is allowed to equilibrate between the respective layers.

Although due to internal migration of the pharmacologically active substance, equilibrium is reached during storage or aging of the device, it is most preferable that the initial load in each layer of the device is such that the equilibrium is established from the beginning, in order to avoid the uncertainty of a lag time between manufacturing and readiness to be used.

BRIEF INTRODUCTION OF THE DRAWINGS

As the present invention is susceptible of being performed in several different ways, some preferred embodiments of the invention are described below. Nevertheless, it should be understood that the present disclosure should considered as an exemplification of the principles of the invention but it is not directed to limit the invention to the examples specifically illustrated.

DESCRIPTION OF THE PREFERRED EMBODIMENTS

Figure 1:
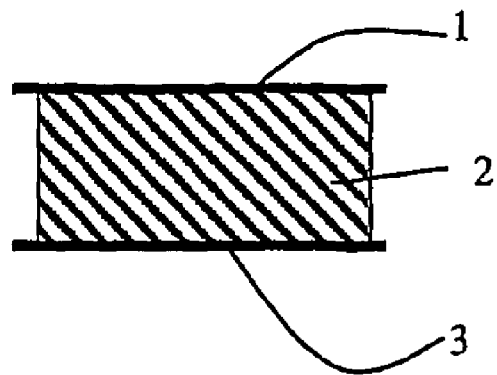
FIG. 1 is a schematic sectional view of a conventional matrix-type transdermal delivery device.

FIG. 1 is a schematic view of a typical conventional matrix-type transdermal delivery device of an active substance that contains a single adhesive layer. The device comprises a backing layer 1 that acts as a protective layer. It comprises also a pressure sensitive adhesive layer 2 that contains the dissolved active drug or drugs and a release liner 3 that is detached before the application of the device onto the skin.

Figure 2:
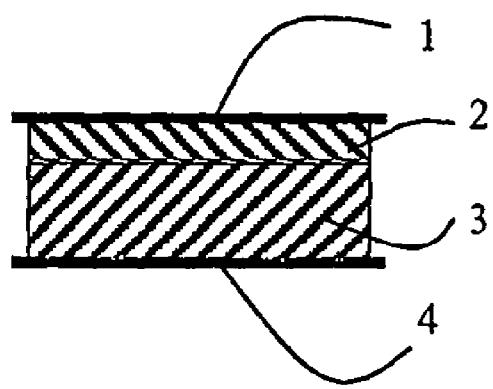
FIG. 2 is a schematic sectional view of a transdermal delivery device of the present invention.

FIG. 2 is a schematic view of a device for the transdermal delivery of drugs, according to the present invention, that comprises two superimposed adhesive layers. The device has a backing layer 1 that is useful as a protective layer for the central portion or matrix of the system. The matrix is composed of two different layers of adhesive matrix: one layer 2 of pressure sensitive adhesive made of for example a functional adhesive, or a blend of a functional and a non-functional adhesive, that contains the active drug or drugs dissolved with or without a permeation enhancer, this layer being superimposed to another adhesive layer 3, made of for example a pressure sensitive non-functional adhesive that has a lower affinity for the drug than the layer 2 and that also contains the active drug or drugs with or without permeation enhancer. The saturation level of the active drug or drugs is similar in both matrix layers. Typically, the device also comprises a release liner 4 that is detached before the application of the device onto the skin.

In these examples, percentages of components are by weight of dry components. Details of the adhesive components employed are given above.

In each example, the concentration of the active substance in the adhesive layers changes as necessary after manufacture due to migration, so that equilibrium is established. In the state of equilibrium the percent saturation in each layer is the same and is less than 100%. We have found that equilibrium is established sufficiently quickly, e.g. in 4 to 5 days.

Example 1

Preparation of a Device with Two Superimposed Layers for the Administration of Fentanyl i) 0.75 g of fentanyl base (USP), 13.6 g of adhesive polymer solution Duro Tak 87-4098 (equivalent to 5.25 g of dry polymer), 14.2 g of adhesive polymer solution Duro Tak 87-2353 (equivalent to 5.25 g of dry polymer) and 1.25 g of lauryl alcohol are placed in a suitable container. Then, the ingredients are stirred with a mechanical stirrer to form a homogeneous and limpid solution.

The coating mixture thus obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 20 μm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 9732). The obtained laminate is picked up on a roll. It will be the second layer of the bilayer device.

ii) Separately, 8 g of fentanyl base (USP), 446.7 g of adhesive polymer solution Duro Tak 87-4098 (equivalent to 172 g of dry polymer) and 20 g of lauryl alcohol are placed in a suitable container. Then the ingredients are stirred with a mechanical stirrer until a homogeneous and limpid solution is obtained. The mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 50 μm). Then, the wet material is conducted through a drying tunnel to eliminate the solvents of the polymeric solution, being inside the tunnel between 5 to 10 minutes at a temperature of about 75° C. The obtained laminate will be the first layer of the bilayer device.

iii) The first layer is laminated on the second one (after the detachment of the release liner 1-5 PESTR 6200-P2 from the second layer). The resultant laminate, that contains now the two adhesive matrix layers is rewound onto a carton core and then the bulk material is die cut to obtain patches with the shape and surface needed. The patches obtained are packed in polyester-aluminium-polyethylene envelopes and stored up to the moment of use.

The device as manufactured thus has the following two layers:

| | % |
|---|---|
| Reservoir layer, 20 μm thickness (2$^{nd}$ layer) | |
| Fentanyl | 6 |
| Lauryl alcohol (LA) | 10 |
| Functional adhesive (FA), —COOH (DT 87-2353) | 42 |
| Non-functional adhesive (N-FA), (DT 87-4098) | 42 |
| Skin contact layer, 50 μm thickness (1$^{st}$ layer) | |
| Fentanyl | 4 |
| Lauryl alcohol (LA) | 10 |
| Non-functional adhesive (N-FA), (DT 87-4098) | 86 |

Adhesive composition of the reservoir layer: 50% FA, 50% N-FA
Adhesive composition of the skin contact layer: 100% N-FA
(Taking into account the thickness of each layer, calculation of the total adhesive composition gives: 14% FA, 86% N-FA)

Example 2

Preparation of a Device with Two Superimposed Layers for the Administration of Fentanyl i) 0.5 g of fentanyl base (USP), 14.6 g of adhesive polymer solution Duro Tak 874098 (equivalent to 5.38 g of dry polymer), 14.2 g of adhesive polymer solution Duro Tak 87-2353 (equivalent to 5.38 g of dry polymer) and 1.25 g of lauryl alcohol are placed in a suitable container. Then, the ingredients are stirred with a mechanical stirrer to form a homogeneous and limpid solution.

The coating mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 20 μm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 9732). The obtained laminate is picked up on a roll. It will be the second layer of the bilayer device.

ii) Separately, 8 g of fentanyl base (USP), 446.7 g of adhesive polymer solution Duro Tak 87-4098 (equivalent to 172 g of dry polymer) and 20 g of lauryl alcohol are placed in a suitable container. Then the ingredients are stirred with a mechanical stirrer until a homogeneous and limpid solution is obtained. The mixture previously obtained is spread in a continuous way on the siliconised face of a siliconised polyester liner (1-5 PESTR 6200-P2) using a knife over roll type coater (the gap between the knife and the roller is adequately set in order to obtain a thickness of dry adhesive matrix of about 50 μm). Then, the coated liner is conducted through a drying tunnel to eliminate the solvents of the polymeric solution, being inside the tunnel between 5 to 10 minutes at a temperature of about 75° C. The obtained laminate will be the first layer of the bilayer device.

iii) The first layer is laminated on the second one (after the detachment of the release liner 1-5 PESTR 6200-P2 from the second layer). The resultant laminate, that contains now the two adhesive matrix layers is rewound onto a carton core and then the bulk material is die cut to obtain patches with the shape and surface needed. The patches obtained are packed in polyester-aluminium-polyethylene envelopes and stored up to the moment of use.

This device as manufactured has the following two layers:—

| | % |
|---|---|
| Reservoir layer, 20 μm thickness (2$^{nd}$ layer) | |
| Fentanyl | 4 |
| LA | 10 |
| FA, —COOH (DT 87-2353) | 43 |
| N-FA, (DT 87-4098) | 43 |

| | % |
|---|---|
| Skin contact layer, 50 μm thickness (1st layer) | |
| Fentanyl | 4 |
| LA | 10 |
| N-FA, (DT 87-4098) | 86 |

Adhesive composition of the reservoir layer: 50% FA, 50% N-PA
Adhesive composition of the skin contact layer: 100% N-FA

Example 3

Preparation of a Device with Two Superimposed Layers for the Administration of Fentanyl The same procedure as in Example 2 is performed, but using in step i) 1 g of fentanyl base (USP), 13.3 g of adhesive polymer solution Duro Talc 87-4098 (equivalent to 5.1 g of dry polymer), 13.9 g of adhesive polymer solution Duro Tak 87-2353 (equivalent to 5.1 g of dry polymer) and 1.25 g of lauryl alcohol.

The device has the following two layers:—

| | % |
|---|---|
| Reservoir layer, 20 μm thickness (2nd layer) | |
| Fentanyl | 8 |
| LA | 10 |
| FA, —COOH (DT 87-2353) | 41 |
| N-FA, (DT 87-4098) | 41 |
| Skin contact layer, 50 μm thickness (1st layer) | |
| Fentanyl | 4 |
| LA | 10 |
| N-FA, (DT 87-4098) | 86 |

Adhesive composition of the reservoir layer: 50% FA, 50% N-FA
Adhesive composition of the skin contact layer: 100% N-FA

Example 4

Preparation of a Device with Two Superimposed Layers for the Administration of Fentanyl The same procedure is as in Example 2, but using in step i) 1.25 g of fentanyl base (USP), 13.0 g of adhesive polymer solution Duro Tak 87-4098 (equivalent to 5.0 g of dry polymer), 13.5 g of adhesive polymer solution Duro Tak 87-2353 (equivalent to 5.0 g of dry polymer) and 1.25 g of lauryl alcohol.

The device as manufactured has the following two layers:—

| | % |
|---|---|
| Reservoir layer, 20 μm thickness (2nd layer) | |
| Fentanyl | 10 |
| LA | 10 |
| FA, —COOH (DT 87-2353) | 40 |
| N-FA, (DT 87-4098) | 40 |
| Skin contact layer, 50 μm thickness (1st layer) | |
| Fentanyl | 4 |
| LA | 10 |
| N-FA, (DT 87-4098) | 86 |

Adhesive composition of the reservoir layer: 50% FA, 50% N-FA
Adhesive composition of the skin contact layer: 100% N-FA

Example 5

Preparation of a Device with Two Superimposed Layers for the Administration of Fentanyl The same procedure as in Example 2 is performed, but using in step i) 0.75 g of fentanyl base (USP), 33.72 g of adhesive polymer solution PIB 4-H: L100 55:45 (equivalent to 8.43 g of dry polymer), 22.78 g of adhesive polymer solution Duro Tak 87-2353 (equivalent to 8.43 g of dry polymer) and 1.125 g of lauryl alcohol and in step ii) 0.50 g of fentanyl base (USP), 88.0 g of adhesive polymer solution PIB 4-H: L100 55:45 (equivalent to 22.0 g of dry polymer) and 2.5 g of lauryl alcohol.

This device as manufactured has the following two layers:

| | % |
|---|---|
| Reservoir layer, 20 μm thickness (2nd layer) | |
| Fentanyl | 4 |
| LA | 6 |
| FA, —COOH (DT 87-2353) | 45 |
| N-FA, (PIB 4H: L 100 55: 45) | 45 |
| Skin contact layer, 50 μm thickness (1st layer) | |
| Fentanyl | 2 |
| LA | 10 |
| N-FA, (PIB 4H: L 100 55: 45) | 88 |

Example 6 (Comparative)

Preparation of a Monolayered Device for the Administration of Fentanyl 0.52 g of fentanyl base (USP), 21.58 g of adhesive polymer solution Duro Tak 87-4098 (equivalent to 8.3 g of dry polymer), 3.67 g of adhesive polymer solution Duro Tak 87-2353 (equivalent to 1.36 g of dry polymer) and 1.13 g of lauryl alcohol are placed in a suitable container. Then, the ingredients are stirred with a mechanical stirrer to form a homogeneous and limpid solution.

The coating mixture obtained is spread in a continuous way on the siliconised face of a siliconised polyester liner (1-5 PESTR 6200-P2) using a knife over roll type coater (the gap between the knife and the roller is adequately set in order to obtain a thickness of dry adhesive matrix of about 70 μm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 9732). The obtained laminate is picked up on a roll and the rolled material is cut to obtain patches with the shape and surface needed. The patches obtained are packed in polyester-aluminium-polyethylene envelopes and stored up to the moment of use.

This device has the single layer:—

| Skin contact layer, 70 µm thickness | % |
|---|---|
| Fentanyl | 4.6 |
| LA | 10 |
| FA, —COOH (DT 87-2353) | 12 |
| N-FA, (DT 87-4098) | 73.4 |

Adhesive composition of the skin contact layer: 14% FA, 86% N-FA

Example 7

Preparation of a Device with Two Superimposed Layers for the Administration of Alfentanyl i) 1.25 g of alfentanyl, 22.7 g of adhesive polymer solution Duro Tak 87-4098 (equivalent to 8.75 g of dry polymer), 7.35 g of adhesive polymer solution Duro Tak 87-2353 (equivalent to 2.5 g of dry polymer) and 1.25 g of n-decanol are placed in a suitable container. Then, the ingredients are stirred with a mechanical stirrer to form a homogeneous and limpid solution.

The coating mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 20 µm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 9732). The obtained laminate is picked up on a roll. It is the second layer of the bilayer device.

ii) Separately, 0.75 g of alfentanyl, 27.2 g of adhesive polymer solution Duro Tak 87-4098 (equivalent to 10.5 g of dry polymer) and 1.25 g of n-decanol are placed in a suitable container. Then the ingredients are stirred with a mechanical stirrer until a homogeneous and limpid solution is obtained. The mixture previously obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 80 µm). Then, the coated liner is conducted through a drying tunnel to eliminate the solvents of the polymeric solution, being inside the tunnel between 5 to 10 minutes at a temperature of about 75° C. The obtained laminate consists of the first layer of the bilayer device.

iii) The first layer is laminated on the second one (after the detachment of the release liner 1-5 PESTR 6200-P2 from the second layer). The resultant laminate, that contains now the two adhesive matrix layers is rewound onto a carton core and then the bulk material is die cut to obtain patches with the shape and surface needed. The patches obtained are packed in polyester-aluminium-polyethylene envelopes and stored up to the moment of use.

Example 8

Preparation of a Device with Two Superimposed Layers for the Administration of Buprenorphine i) 1.0 g of buprenorphine, 11.3 g of adhesive polymer solution Duro Tak 87-4098 (equivalent to 4.35 g of dry polymer), 19.2 g of adhesive polymer solution Duro Tak 87-2353 (equivalent to 6.525 g of dry polymer) and 0.625 g of myristyl alcohol are placed in a suitable container. Then, the ingredients are stirred with a mechanical stirrer to form a homogeneous and limpid solution.

The coating mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 30 µm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 9732). The obtained laminate is picked up on a roll. It will be the second layer of the bilayer device.

ii) Separately, 0.5 g of buprenorphine, 29.5 g of adhesive polymer solution Duro Tak 87-4098 (equivalent to 11.375 g of dry polymer) and 0.625 g of myristyl alcohol are placed in a suitable container. Then the ingredients are stirred with a mechanical stirrer until a homogeneous and limpid solution is obtained. The mixture obtained is spread in a continuous way on the siliconised face of a siliconised polyester liner (1-5 PESTR 6200-P2) using a knife over roll type coater (the gap between the knife and the roller is adequately set in order to obtain a thickness of dry adhesive matrix of about 60 µm). Then, the coated liner is conducted through a drying tunnel to eliminate the solvents of the polymeric solution, being inside the tunnel between 5 to 10 minutes at a temperature of about 75° C. The obtained laminate is the first layer of the bilayer.

iii) The first layer is laminated on the second one (after the detachment of the release liner 1-5 PESTR 6200-P2 from the second layer). The resultant laminate, that contains now the two adhesive matrix layers is rewound onto a carton core and then the bulk material is die cut to obtain patches with the shape and surface needed. The patches obtained are packed in polyester-aluminium-polyethylene envelopes and stored up to the moment of use.

Example 9

Preparation of a Device with Two Superimposed Layers for the Administration of Sufentanyl i) 0.5 g of sufentanyl, 31.8 g of adhesive polymer solution Duro Tak 87-4098 (equivalent to 12.25 g of dry polymer), 33.1 g of adhesive polymer solution Duro Tak 87-2353 (equivalent to 12.25 g of dry polymer) are placed in a suitable container. Then, the ingredients are stirred with a mechanical stirrer to form a homogeneous and limpid solution.

The coating mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 20 µm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 9732). The obtained laminate is picked up on a roll. It will be the second layer of the bilayer device.

ii) Separately, 0.15 g of sufentanyl, 38.1 g of adhesive polymer solution Duro Tak 87-4098 (equivalent to 14.7 g of dry polymer) and 0.15 g of glyceryl monooleate are placed in a suitable container. Then the ingredients are stirred with a mechanical stirrer until a homogeneous and limpid solution is obtained. The mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 60 μm). Then, the coated liner is conducted through a drying tunnel to eliminate the solvents of the polymeric solution, being inside the tunnel between 5 to 10 minutes at a temperature of about 75° C. The obtained laminate is the first layer of the bilayer.

iii) The first layer is laminated on the second one (after the detachment of the release liner 1-5 PESTR 6200-P2 from the second layer). The resultant laminate, that contains now the two adhesive matrix layers is rewound onto a carton core and then the bulk material is die cut to obtain patches with the shape and surface needed. The patches obtained are packed in polyester-aluminium-polyethylene envelopes and stored up to the moment of use.

Example 10

Preparation of a Device with Two Superimposed Layers for the Administration of Nicotine i) 6.0 g of nicotine, 56.8 g of adhesive polymer solution Duro Tak 87-4098 (equivalent to 21.0 g of dry polymer), 17.6 g of adhesive polymer solution Duro Tak 87-2287 (equivalent to 9.0 g of dry polymer) are placed in a suitable container. Then, the ingredients are stirred with a mechanical stirrer to form a homogeneous and limpid solution.

The coating mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 50 μm).

Then, the coated liner is conducted through a drying tunnel to eliminate the solvents of the polymeric solution, being inside the tunnel between 5 to 10 minutes at a temperature of about 75° C. Finally the liner coated with the adhesive layer is laminated with an ethyl-vinyl acetate and polyester liner (Scotchpack 1109). The obtained laminate is picked up on a roll. It will be the second layer of the bilayer device.

ii) Separately, 3.0 g of nicotine, 64.7 g of adhesive polymer solution Duro Tak 87-2287 (equivalent to 33.0 g of dry polymer) and 4.0 g of polyethylene glycol 400 are placed in a suitable container. Then the ingredients are stirred with a mechanical stirrer until a homogeneous and limpid solution is obtained. The mixture obtained is spread in a continuous way on the siliconised face of a siliconised polyester liner (1-5 PESTR 6200-P2) using a knife over roll type coater (the gap between the knife and the roller is set in order to obtain a thickness of dry adhesive matrix of about 50 μm). Then, the coated liner is conducted through a drying tunnel to eliminate the solvents of the polymeric solution, being inside the tunnel between 5 to 10 minutes at a temperature of about 75° C. The obtained laminate is the first layer of the bilayer device.

iii) The first layer is laminated on the second one (after the detachment of the release liner 1-5 PESTR 6200-P2 from the second layer). The resultant laminate, that contains now the two adhesive matrix layers is rewound onto a carton core and then the bulk material is die cut to obtain patches with the shape and surface needed. The patches obtained are packed in polyester-aluminium-polyethylene envelopes and stored up to the moment of use.

Example 11

Dissolution Profile of a Device According to the Present Invention

Figure 3:
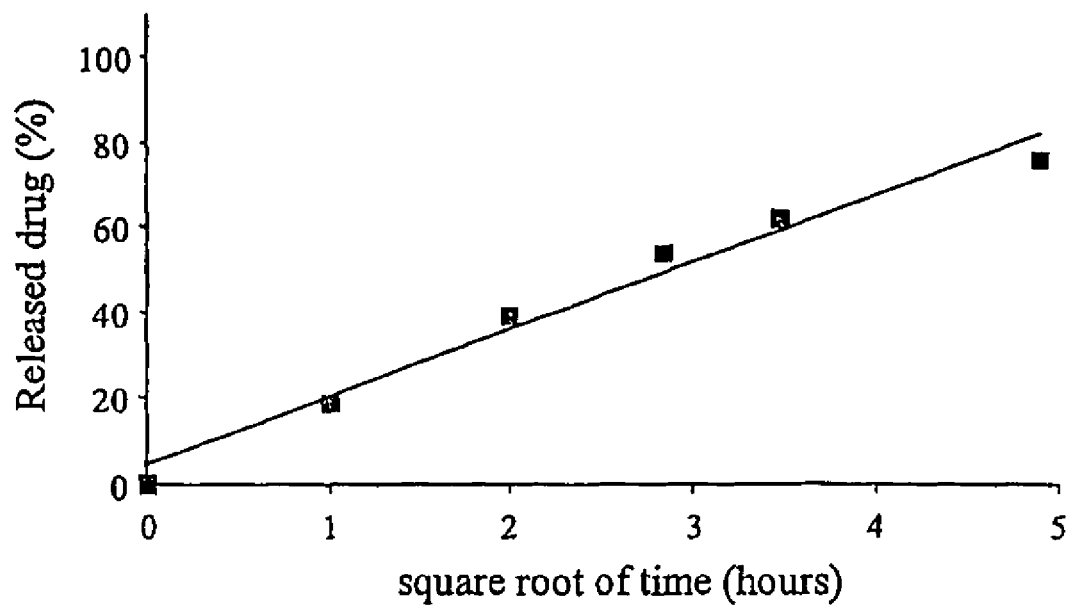
FIGS. 3 to 8 are graphs showing release profiles of drugs from devices described in the Examples.

The dissolution profile of a bilayered device manufactured according to example 1 was performed. For this assay, a dissolution test apparatus (US Pharmacopoeia) was used. Samples were collected at 1, 4, 8, 12 and 24 hours after the start of the experiment and fentanyl content was analysed by HPLC using a suitable technique. The corresponding profile is in FIG. 3.

The drug delivery from a transdermal matrix device is governed by the diffusion of the solute within the matrix. According to the accepted Higuchi's kinetic model (Transdermal and Topical Drug Delivery Systems, edited by T. K Ghosh, W. R. Pfister and S. I. Yum, Interpharm Press Inc., USA, 1997, pp. 159-166), the delivery rate equation is based on Fick's diffusion laws and predicts a linear relationship between the amount of drug delivered by area unit and the square root of the time. From the obtained results, it is seen that the superimposition of layers with different affinity for the active drug provides a transdermal system that behaves according to Higuchi's kinetic model.

Example 12

Comparison of the Dissolution Profile Between a Device According to the Present Invention and a Device with the Same Polymeric Composition Coated as a Single Layer The dissolution profiles of two devices were compared: one was a bilayer device manufactured according to example 1 and the other a monolayer device manufactured according to example 6. In particular, the device according to example 6 contains the same total composition of each ingredient as the bilayer device according to the present invention, with the difference that they are distributed in a single layer. The compared devices have the same total thickness and surface. The compositions of the used devices are summarised in the following table:

| Type of device | Total mg of active substance (fentanyl) | Total mg of FA (DT 87-2353) | Total mg of N-FA (DT 87-4098) |
|---|---|---|---|
| Bilayer, ex. 1 | 6.4 | 16.8 | 102.8 |
| Monolayer, ex. 6 | 6.4 | 16.8 | 102.8 |

Figure 4:
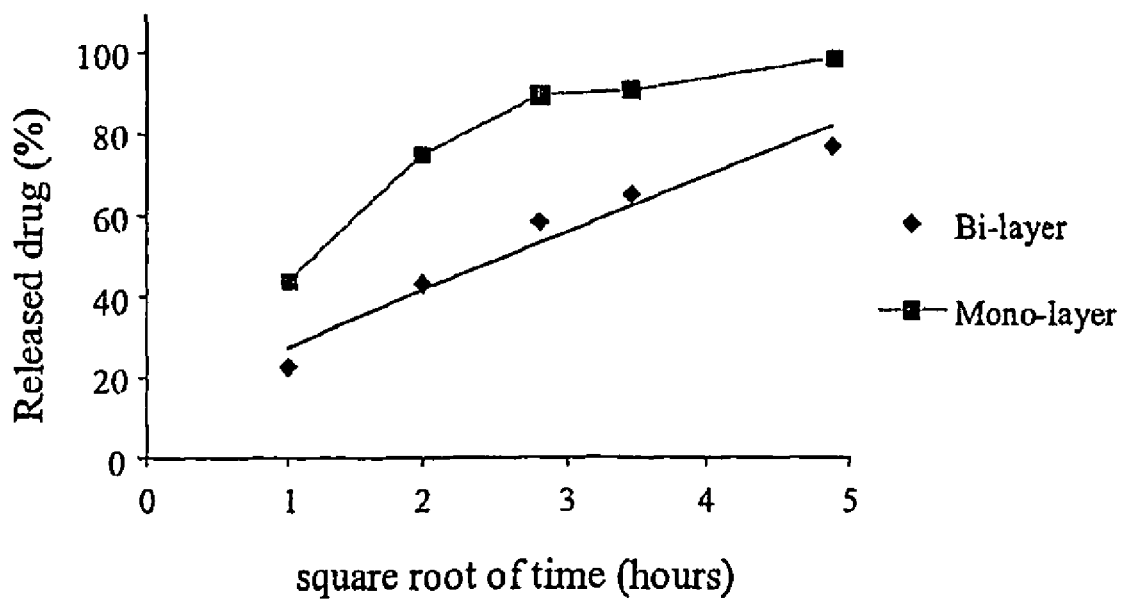

For the present assay a dissolution test apparatus no 5 (US Pharmacopoeia) was used. Samples were collected at 1, 4, 8, 12 and 24 hours after the start of the experiment and fentanyl content was analysed by HPLC using a suitable technique. The corresponding delivery profiles are in FIG. 4.

As was demonstrated in the previous example, the superimposition of layers with different affinity for the active drug allows to obtain a transdermal system that behaves according to Higuchi's kinetic model, while the monolayer matrix device does not fulfil that model in the period of time considered.

Besides, for the same total composition, the presence of the components distributed in a bilayer arrangement allow a control of the delivery of the active drug that is not obtained by the mixture of the same component arranged in a single layer.

Example 13

Permeation Profile of a Device According to the Present Invention

Permeation was performed using a device manufactured according to example 1.

Figure 5:
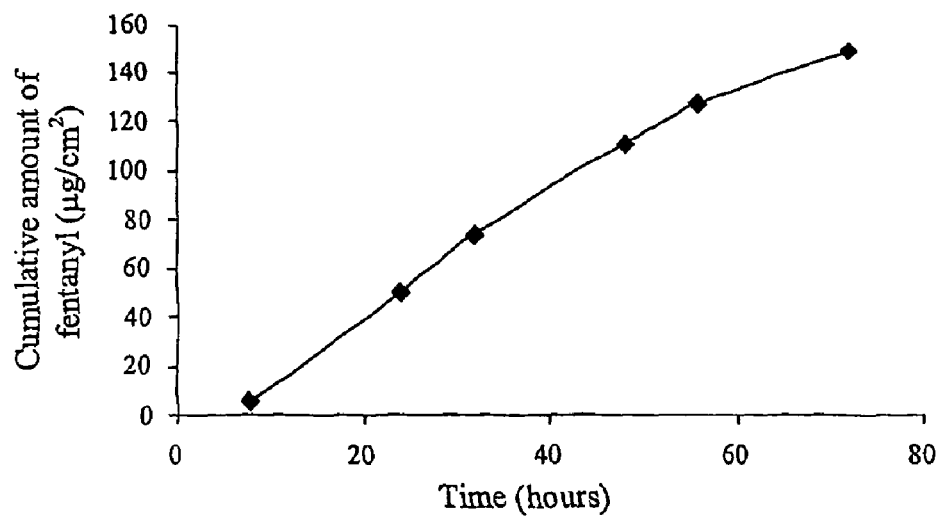

Measurements were performed by triplicate using Valia-Chien type cells, with constant stirring in a water bath with a fixed temperature (34° C.). Circular pieces of human female intact skin (stratum corneum, epidermis and dermis) with 2 cm diameter and 300 lam thickness were used. The solution used consisted of 5.5 ml of a phosphate buffer isotonic solution adjusted to pH=6.0. Samples were collected at 24, 32, 48, 56 and 72 hours after the start of the experiment and fentanyl content was analysed by HPLC using a suitable technique. The results obtained are shown in FIG. 5.

It is observed that the device according to the present invention shows a permeation rate that remains constant up to 72 hours.

Example 14

Comparison of the Dissolution Profile of a Commercial Reservoir-Type Device (Duragesic®) and Devices of Different Sizes According to Examples 1 and 3 of the Present Invention The sizes and contents of the devices used are shown in the following table:

| Type of device | Active surface (cm²) | Total surface (cm²) | Total mg of active substance (fentanyl) |
|---|---|---|---|
| Example 1 | 20 | 20 | 6.3 |
| Example 1 | 10 | 10 | 3.15 |
| Example 1 | 5 | 5 | 1.58 |
| Example 3 | 20 | 20 | 7.3 |
| Example 3 | 10 | 10 | 3.65 |
| Example 3 | 5 | 5 | 1.83 |
| Duragesic | 20 | 34 | 5 |

Figure 6:
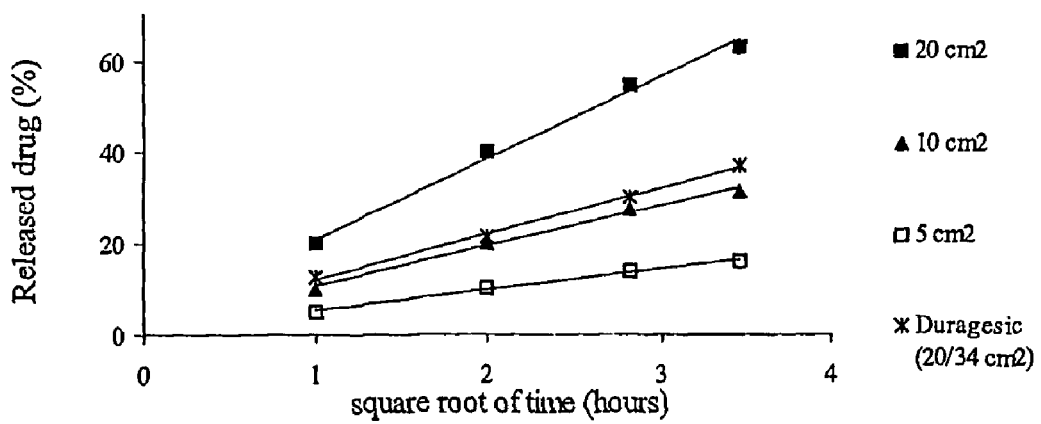
Figure 7:
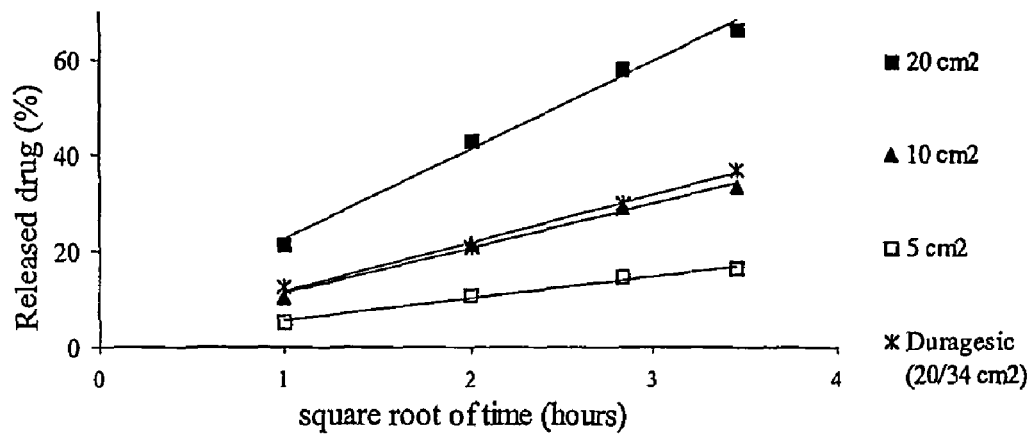

For the present assay a dissolution test apparatus No 5 (US Pharmacopeia) was used. Samples were collected at 1, 4, 8 and 12 hours after the start of the experiment and fentanyl content was analysed by HPLC using a suitable technique. The obtained results, expressed as percentages of drug delivery vs. square Toot of time, are shown in FIG. 6 for the devices of Example 1 compared with Duragesic and FIG. 7 for the devices of Example 3 compared with Duragesic:

From these obtained results, it is shown that by means of the devices of the present invention, a useful transdermal patch for the administration of drugs can be obtained. The mentioned device does not require a rate controlling membrane, and it has a suitable performance with a lower load of drug and a smaller surface than a commercial fentanyl patch reservoir-type device with rate controlling membrane (Duragesic®), while it also provides a delivery profile that is equivalent to the mentioned commercial device. Particularly, from the data of this example, it is shown that, according to the present invention, it is possible to obtain a patch for the transdermal administration of fentanyl that has an active area of approximately half and a total area smaller than a third, compared to a commercial fentanyl device (Duragesic®), containing approximately 30% less active substance and providing an equivalent delivery.

Example 15

Comparison of the Dissolution Profiles of Different Devices According the Present Invention The dissolution profiles of different bilayered devices according to the present invention was performed. They all have the same adhesive composition, thickness and size, while their initial fentanyl concentration in the second layer is different.

For the present assay a dissolution test apparatus No 5 (US Pharmacopeia) was used. Samples were collected at 1, 4, 8 and 12 hours after the start of the experiment and fentanyl content was analysed by HPLC using a suitable technique. The initial active substance composition (expressed as weight percentages of each layer) of the used devices are detailed in the following table:

| | Percentile composition of the active substance (fentanyl) | |
|---|---|---|
| Type of device | initial fentanyl % in the $1^{st}$ layer | initial fentanyl % in the $2^{nd}$ layer |
| Example 2 | 4% | 4% |
| Example 1 | 4% | 6% |
| Example 3 | 4% | 8% |
| Example 4 | 4% | 10% |

Figure 8:
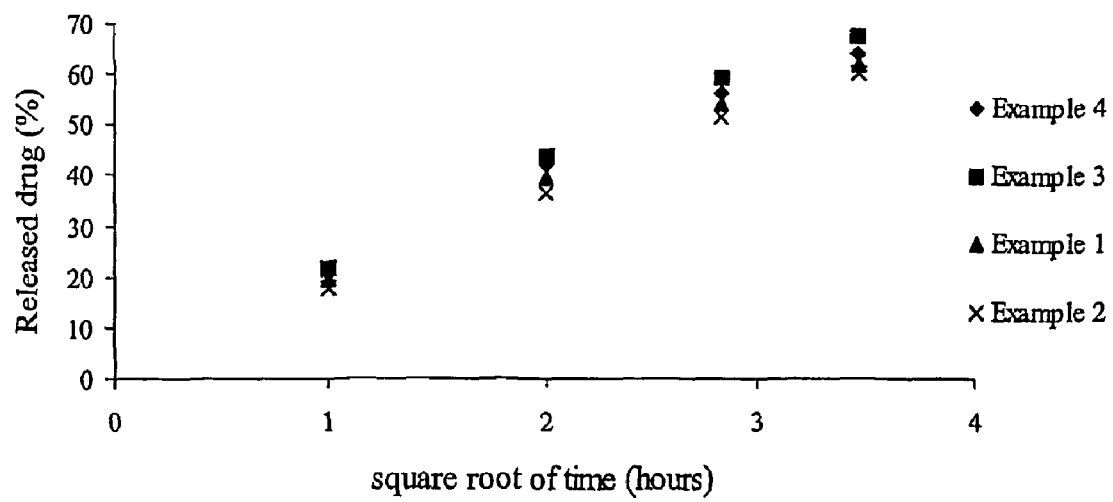

The profiles are shown in FIG. 8:

By the results obtained it is shown that when the loading of drug is increased in the second layer, the behaviour of the devices still fulfil Higuchi's kinetics model.

Example 16

Adhesive Properties of Different Devices According to the Present Invention

In vitro adhesive properties of devices according to examples 1 to 4 were studied. The studied properties were measured through the assays of "tack", "adhesiveness" and "shear adhesion". "Tack" is expressed as the distance a stainless steel roller rolls on the adhesive surface, when it is rolled down in an inclined ramp at standard height and inclination. Both "adhesiveness" and "shear adhesion" of the adhesive matrix are determined using a test bank that consists of a holding for ten stainless steel plates whose angle from vertical can vary (for the "adhesiveness" assay a 90° angle was used, while for the "shear adhesion" a 2° one was used). The patches to be tested are applied to the plated places in the holding, a weight is fixed to the free side of the patch and the time needed to detach the patch from the plate is measured. The assay is performed in triplicate and the average of the measured values is informed. The obtained results are grouped in the following table:

| Type of device | Tack | Adhesiveness | Shear adhesion |
| --- | --- | --- | --- |
| Example 2 | 70 mm | 1 min 48 sec | 11 min 8 sec |
| Example 1 | 58 mm | 1 min 37 sec | 8 min 40 sec |
| Example 3 | 55 mm | 1 min 38 sec | 7 min 7 sec |
| Example 4 | 47 mm | 1 min 41 sec | 9 min 52 sec |

From these results a suitable in vivo adhesive performance can be predicted and, in consequence, the behaviour that the device will show during its application in human beings.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A Transdermal delivery device for the transdermal delivery of an active substance, including a pharmaceutically active substance, the device comprising:
   a. a release layer detachable when the device is used;
   b. a first pressure sensitive adhesive layer, coated over the release layer;
   c. a second adhesive layer, coated over said first layer; the ratio of the thickness of the first layer to the thickness of the second layer being in the range of 1.2-7:1;
   d. a backing layer, coated over said second adhesive layer substantially impermeable to the active substance; and
   wherein the first and second layers comprise a polymer selected individually from the group consisting of acrylic polymers, polyisobutylenes and silicone elastomers;
   wherein:
   1. the first layer is adapted to be brought into contact with the skin;
   2. the active substance is present and dissolved in both of said first and second layers;
   3. the affinity of said first layer for the active substance is between about 1.15 and about 10 times lower than that of said second layer;
   4. the percent saturation of said active substance in both of said first and second layers is the same and both are less than 100%; and
   5. the second layer replenishes the first layer, as the active substance is delivered to a patient, and the combination of the relative thicknesses of the first and second layers and their relative affinities for the active substance determines the delivery profile, achieving a highly constant efflux rate during use.

2. A transdermal delivery device according to claim 1 wherein the thickness of each said layer when dry is in the range 5 to 150 μm.

3. A transdermal delivery device according to claim 2 wherein the thickness of the first layer when dry is in the range 5 to 125 μm and the thickness of the second layer when dry is in the range 5 to 75 μm.

4. A transdermal delivery device according to claim 1 wherein the affinity of said first layer for said active substance is 1.15 to 1.75 times lower than that of said second layer.

5. A transdermal delivery device according to claim 1 wherein said first layer has a polymer matrix consisting of at least one non-functional polymer component and said second layer has a polymer matrix consisting of at least one functional polymer component or a mixture of functional and non-functional polymer components.

6. A transdermal delivery device according to claim 5 wherein said second layer is composed of about 10 to about 90% of at least one functional polymer component and about 90 to about 10% of at least one non-functional polymer component, percentages being expressed relative to total weight of dry layer.

7. A transdermal delivery device according to claim 6 wherein said second layer is composed of about 20 to about 50% of at least one functional polymer component and about 50 to about 80% of at least one non-functional polymer component, percentages being expressed relative to total weight of dry layer.

8. A transdermal delivery device according to claim 5 wherein the or each said functional polymer component of said second layer has functional groups selected from —COOH and —OH.

9. A transdermal delivery device according to claim 1 wherein each of the first and second layers comprise one or more acrylic polymer components.

10. A transdermal delivery device according to claim 1 wherein at least one of the first and second layers comprises at least one permeation enhancer.

11. A transdermal delivery device according to claim 10 wherein the amount of permeation enhancer in each of said layers, expressed as percent of the dry weight of each layer, is between 3.5 and 22%.

12. A transdermal delivery device according to claim 1 wherein the pharmacologically active substance is selected from fentanyl, alfentanyl, sufentanyl, carfentanyl, lofentanyl, and buprenorphine.

13. A transdermal delivery device according to claim 1 wherein the pharmacologically active substance is nicotine or one of its pharmaceutically acceptable salts.

14. A transdermal delivery device according to claim 1 wherein the pharmacologically active substance is fentanyl or one of its pharmaceutically acceptable salts.

15. A transdermal delivery device according to claim 14 wherein a permeation enhancer is present and is a saturated fatty alcohol.

16. A transdermal delivery device according to claim 15 wherein the saturated fatty alcohol is lauryl alcohol.

17. A transdermal delivery device according to claim 14 wherein the first layer to be in intimate contact with the skin is loaded with a fentanyl base content of 2 to 4%, expressed as percentage of the dry weight of said first layer.

18. A transdermal delivery device according to claim 14 wherein the second layer is loaded with a fentanyl base content of 4 to 10%, expressed as percentage of the dry weight of said second layer.

19. A transdermal delivery device according to claim 14 having a concentration between 5 and 15% of lauryl alcohol in each of said layers, percentage expressed as dry weight of each of the layers.

20. A transdermal delivery device according to claim 14 adapted to release a therapeutically effective dose of the active substance during at least three days.

21. A process for the manufacture of a device for the transdermal administration of an active substance according to claim 1, which comprises the following steps:
   a. coating and drying a first precursor adhesive layer containing the active substance that will be the second layer of said device onto a temporary release liner;
   b. laminating said first precursor adhesive layer together with the temporary release film onto a backing layer;

c. coating and laminating onto a final release liner a second precursor adhesive layer containing the active substance that will be the first layer of said device; and d. detaching the temporary release film and laminating said second precursor adhesive layer adhered to the final release liner obtained in (c) to said first precursor adhesive layer obtained in (b) that is adhered to the backing layer.

22. A process according to claim 21, wherein the respective amounts of said active substance in said first and second precursor adhesive layers differ from the amounts in said device when ready for use, and after step (d) the active substance is allowed to equilibrate its percent saturation between the respective layers.

* * * * *